United States Patent [19]

Lecoufle et al.

[11] Plant 4,838

[45] Apr. 13, 1982

[54] ODONTIODA ORCHID PLANT

[75] Inventors: Maurice Lecoufle; Michel Vacherot, both of Boissy St. Leger, France

[73] Assignee: Les Petite Fils et Fils de Vacherot & Lecoufle, Boissy St. Leger, France

[21] Appl. No.: 151,945

[22] Filed: May 21, 1980

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Chas. W. Rummler

[57] ABSTRACT

A new and distinct variety of orchid plant of the Odontioda genus particularly distinguished by the distinctive shape and red-brown coloring of its medium sized flowers, of which ten to fifteen are borne on each item, alternately spaced at two to four centimeters intervals along the upper half of the stem length, and by its regular fall and winter flowering under environmental conditions like those of Paris, France.

2 Drawing Figures

ORIGIN OF THE NEW PLANT

Our new orchid plant originated as a seedling of the variety Odontioda Henriette Lecoufle, which resulted from the cross of Odontioda Balek × Odontoglossum Pacha which was made by us at Boissy St. Leger in the course of breeding efforts which we have carried on for more than twenty years with the object of producing good cultivars of Odontiodas having flowers of large size, good shape and improved coloring. This variety was selected for propagation and trial because of the shape and color of its flowers and our continued meristem propagation of this new variety, through successive generations at Boissy St. Leger, has demonstrated that its distinctive characteristics hold true from generation to generation and appear to be firmly fixed.

DESCRIPTION OF THE DRAWING

This new variety of orchid plant is illustrated by the accompanying full color photographic drawing which shows a face view of one of the flowers, the color reproduction being as true as is reasonably possible to obtain by commercial photographic procedures, and by a second drawing which shows the general dimensions and form of the flower.

DESCRIPTION OF THE NEW VARIETY OF ORCHID PLANT

The following is a detailed description of our new variety of orchid plant with color designations according to The R.H.S. Colour Chart published by The Royal Horticultural Society of London, England.

THE PLANT

Origin: Seedling of Oda. Henriette Lecoufle.

Parentage:

*Seed parent.*—Oda. Balek.

*Pollen parent.*—Odm. Pacha.

Classification:

*Botanic.*—Odontioda hybrid.

*Commercial.*—Odontioda mericlone.

Form: Herbaceous.

Height: From 20 to 60 cm. according to the age of the plant.

Bulbs:

*Number.*—A plant is adult when it has three well formed bulbs with leaves.

*Size.*—The front bulb of the adult plant is about 4.5 cm. wide and 5.5 cm. high.

*Stems.*—The primary bulbs can bear one or two stems.

*Leaves.*—Number: Generally the front bulb has four leaves, two from the apex and one from each side plus several embryonic leaves on each side. The other bulbs also have four leaves but the old bulbs then lose their leaves beginning with those on the sides. Length: From 20 to 30 cm.

THE FLOWER

Blooming habit: Recurrent. This variety begins to flower whenever new growth is completed and thereafter flowers regularly in fall or during winter under the environmental conditions of Paris, France. In more tropical areas, the plant may bloom two or three times a year.

Number of flowers: From 10 to 15 per stem.

Borne: The first flower occurs about halfway from the base of the stem and thereafter the flowers are alternately spaced at 2 to 4 cm. intervals. Each flower is carried on a pedicel varying in length from 2.5 cm. to 3 cm.

Average size of flower:

*Width.*—About 8.8 cm.

*Height.*—About 8.3 cm.

*Width across the two lateral sepals.*—About 7 cm.

*Width of the dorsal sepal.*—About 3.5 cm.

*Width of each petal.*—About 4.5 cm.

*Width of the labellum.*—About 2.5 cm.

*Height of the labellum.*—About 3 cm.

*Length of the gynostemium.*—About 1.8 cm. The petals are much larger than the sepals but are all of good round shape.

Color:

*Petals and sepals.*—Greyed Orange RHS 175D bordered by a fringed margin of pure White and having some Magenta marks of Red-Purple RHS 66D. The central portion of the tip ends have a light Magenta overcast extending into the White margin. The White base of the sepals (not shown) meets a dark Red-Brown color like RHS 181A which rapidly disappears in the Brown Oranged (RHS 175D) color of the main body.

*Labellum.*—The Greyed Orange RHS 175D body is bordered by a very fine White line and the tip end portion is fringed and pure White. The throat is Straw Yellow RHS 14A with dark Red-Brown streaks extending from the central portion of the body toward the gynostemium and the gynostemium has spots of the same dark Red-Brown color.

We claim:

1. A new Odontioda orchid plant substantially as herein shown and described, distinguished in particular by its distinctive shape and the red-brown oranged coloring of the sepals, petals and labellum, and by the fringed white margins and tip ends of the petals and labellum.

* * * * *

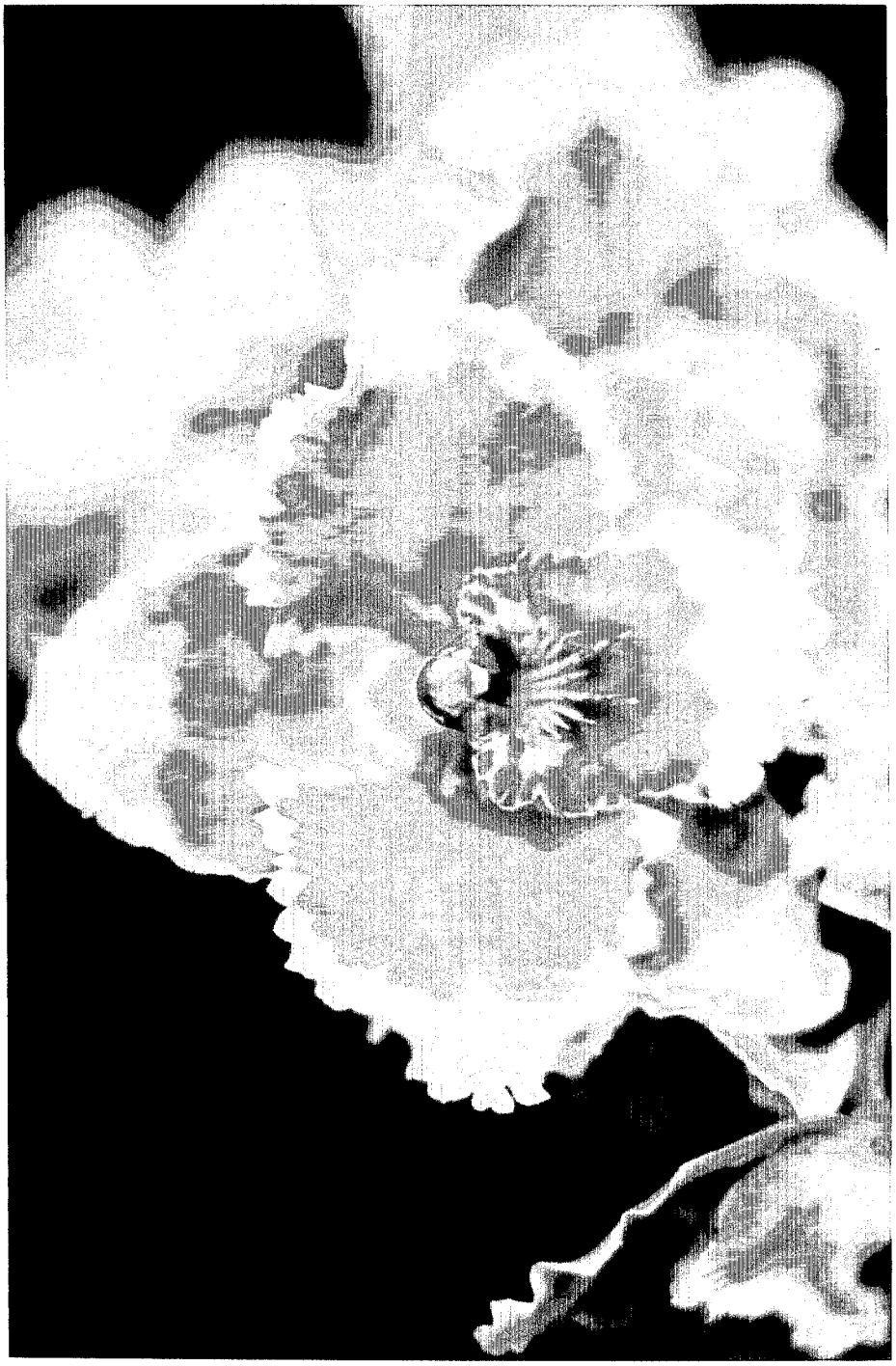

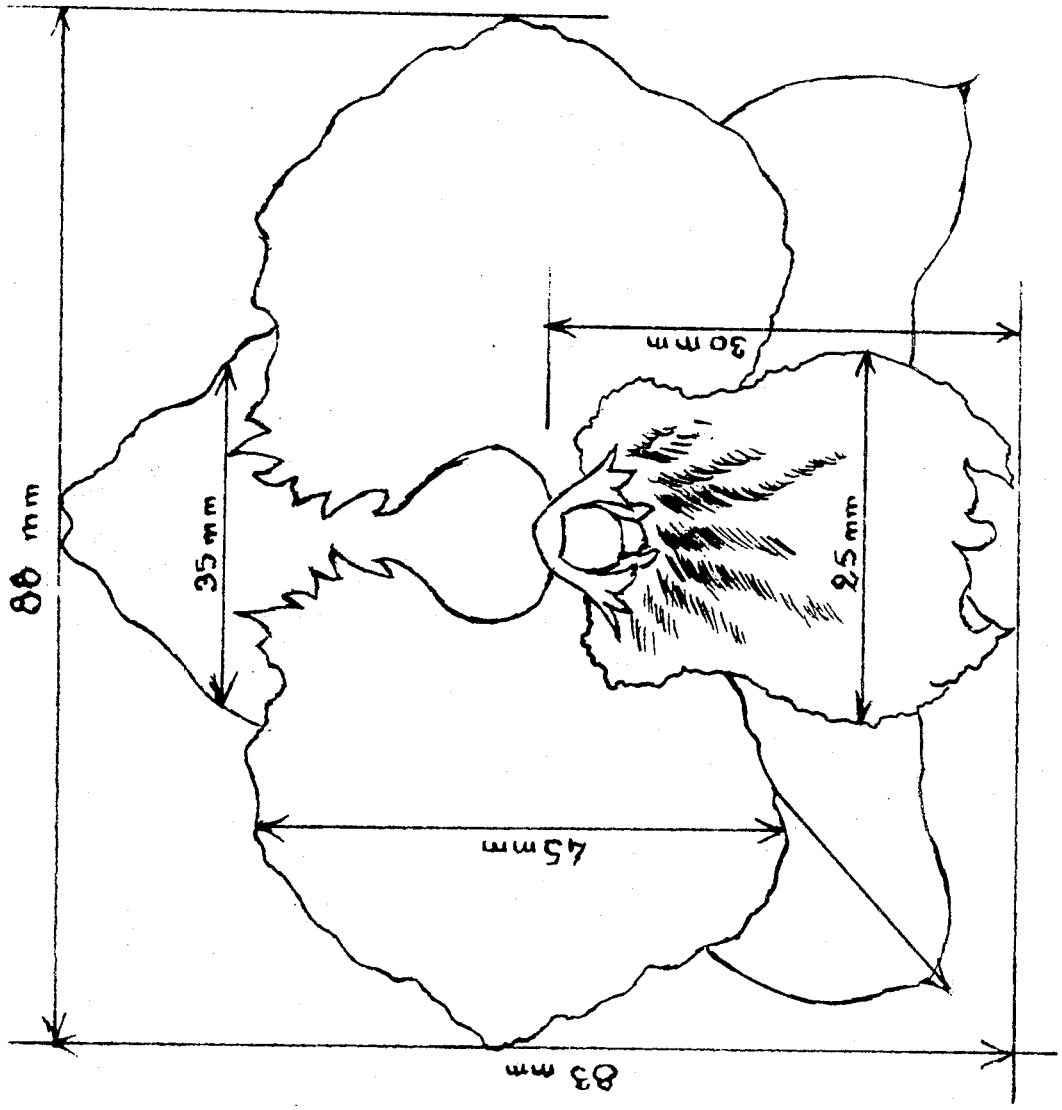
88 mm
35 mm
83 mm
45mm
25mm
30mm